US006887267B2

(12) United States Patent
Dworschak et al.

(10) Patent No.: US 6,887,267 B2
(45) Date of Patent: May 3, 2005

(54) INSERTION CATHETER FOR VASCULAR PROSTHESIS

(75) Inventors: Manfred Dworschak, Duerbheim (DE); Theodor Lutze, Balgheim (DE); Thomas Weik, Tuttlingen (DE); Dieter Weisshaupt, Immendingen (DE); Jens-Rainer Allenberg, Heidelberg (DE)

(73) Assignee: Aesculap AG & Co. KG, Tuttlingen (DE)

( * ) Notice: Subject to any disclaimer, the term of this patent is extended or adjusted under 35 U.S.C. 154(b) by 406 days.

(21) Appl. No.: 10/060,042

(22) Filed: Jan. 29, 2002

(65) Prior Publication Data

US 2002/0165554 A1 Nov. 7, 2002

Related U.S. Application Data

(63) Continuation of application No. PCT/EP00/07354, filed on Jul. 29, 2000.

(30) Foreign Application Priority Data

Aug. 5, 1999 (DE) .......................................... 199 36 980

(51) Int. Cl.⁷ ............................... A61F 2/06; A61F 2/24
(52) U.S. Cl. ...................... 623/1.23; 623/1.11; 606/108
(58) Field of Search .................. 606/108; 623/1.11, 623/1.23

(56) References Cited

U.S. PATENT DOCUMENTS 5,683,451 A    11/1997  Lenker et al.
5,690,644 A    11/1997  Yurek et al.
5,746,745 A     5/1998  Abele et al.
5,879,380 A     3/1999  Kalmann et al.
6,398,802 B1 *  6/2002  Yee ............................ 623/1.13
6,565,594 B1 *  5/2003  Herweck et al. ........... 623/1.11
6,579,305 B1 *  6/2003  Lashinski ................... 623/1.11
6,610,085 B1 *  8/2003  Lazarus ..................... 623/1.11

FOREIGN PATENT DOCUMENTS

DE    93 21 003        9/1995
DE    197 13 280      10/1998
EP    0 554 579        8/1993
EP    0 820 784        1/1998
WO    WO 98/09583      3/1998
WO    WO 98/20812      5/1998

* cited by examiner

*Primary Examiner*—Vy Bui
(74) *Attorney, Agent, or Firm*—Barry R. Lipsitz; Douglas M. McAllister

(57) ABSTRACT

With an insertion catheter for inserting a vascular prosthesis into a vessel, with an elongate, substantially tubular catheter cover having a proximal and a distal end, with an outlet for the vascular prosthesis provided at the distal end, in order to make insertion of the vascular prosthesis into the vessel particularly safe and simple, in particular, to provide the vascular prosthesis with protection against twisting, it is proposed that the outlet have a cross-sectional shape differing from a circular shape, and that the cross-sectional area defined by the outlet area be smaller than the cross-sectional area of the vascular prosthesis inserted in the vessel in the opened, unexpanded state.

47 Claims, 4 Drawing Sheets

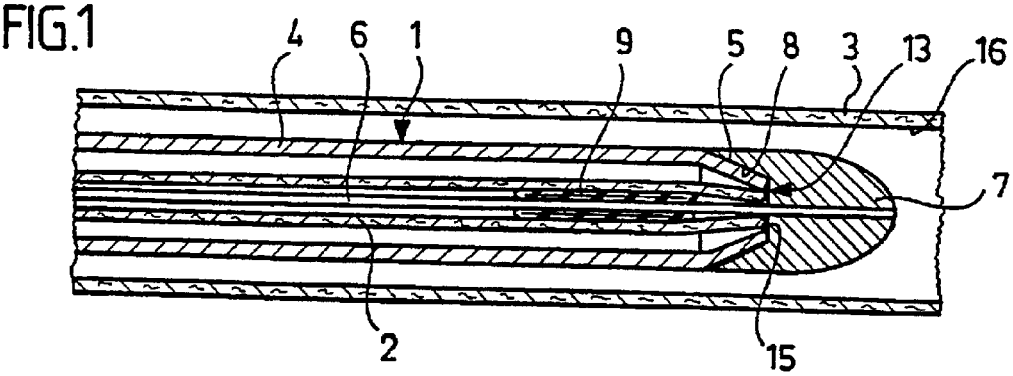
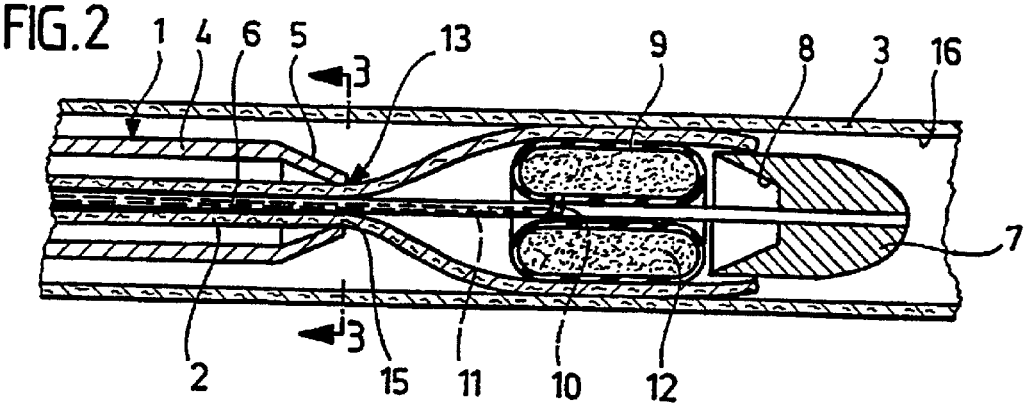
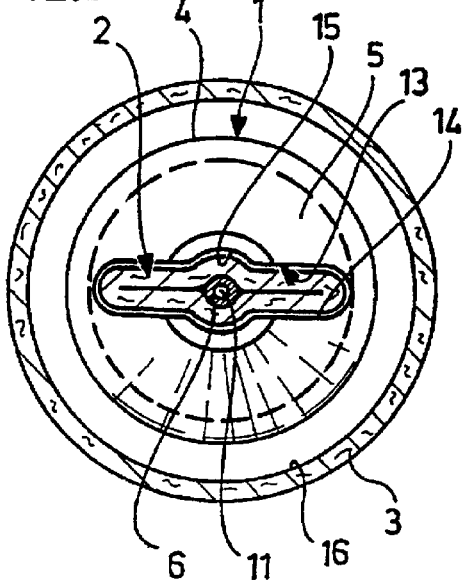
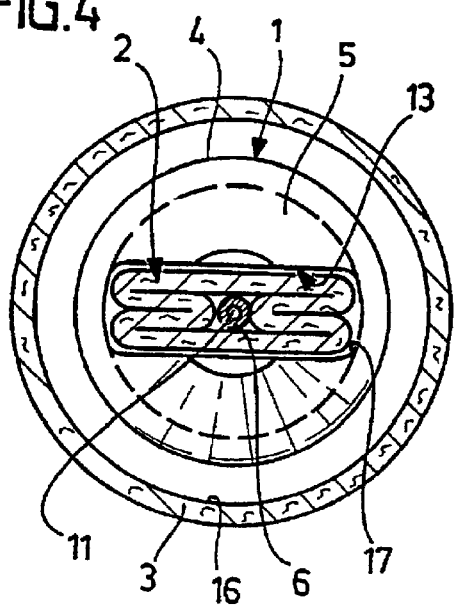

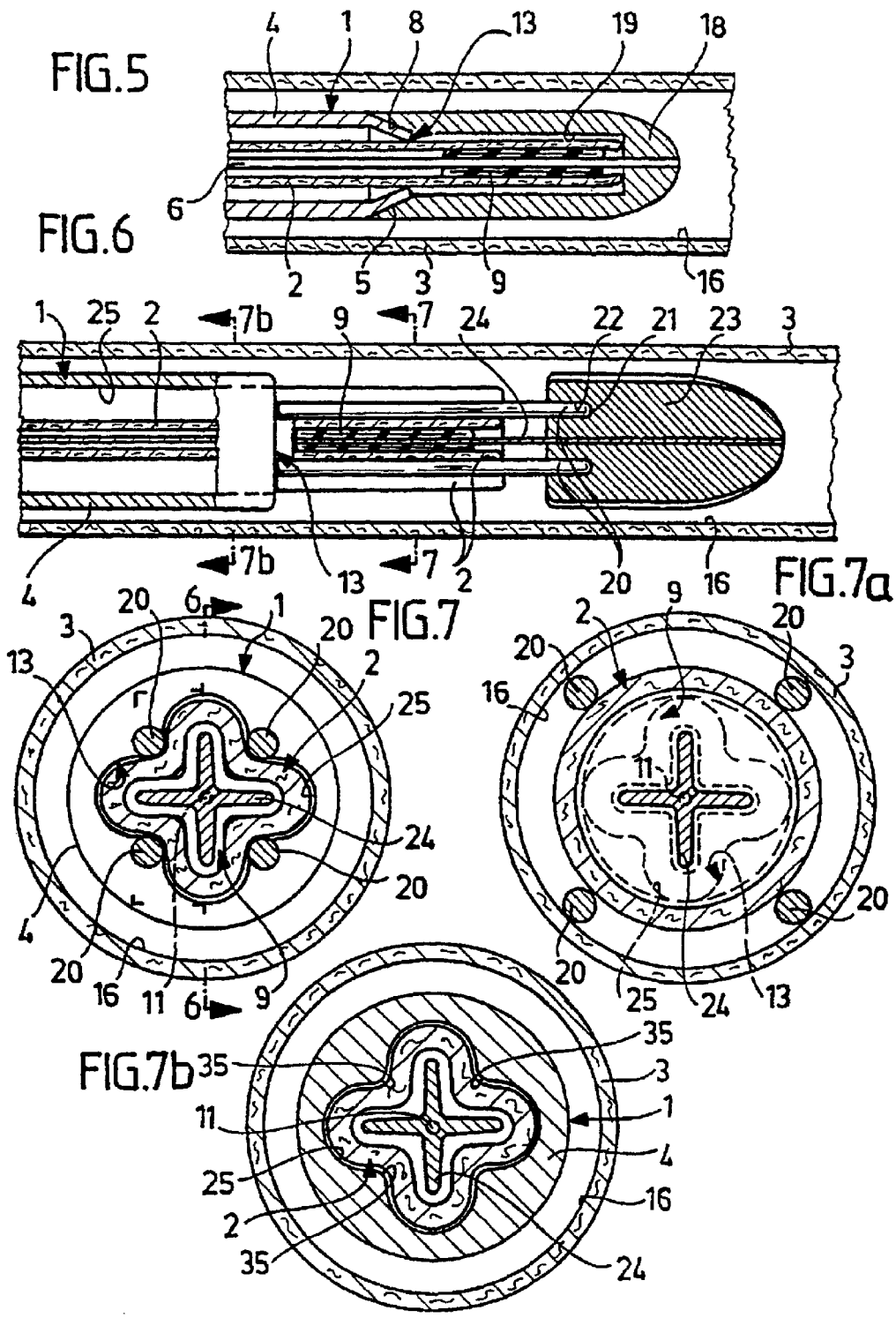

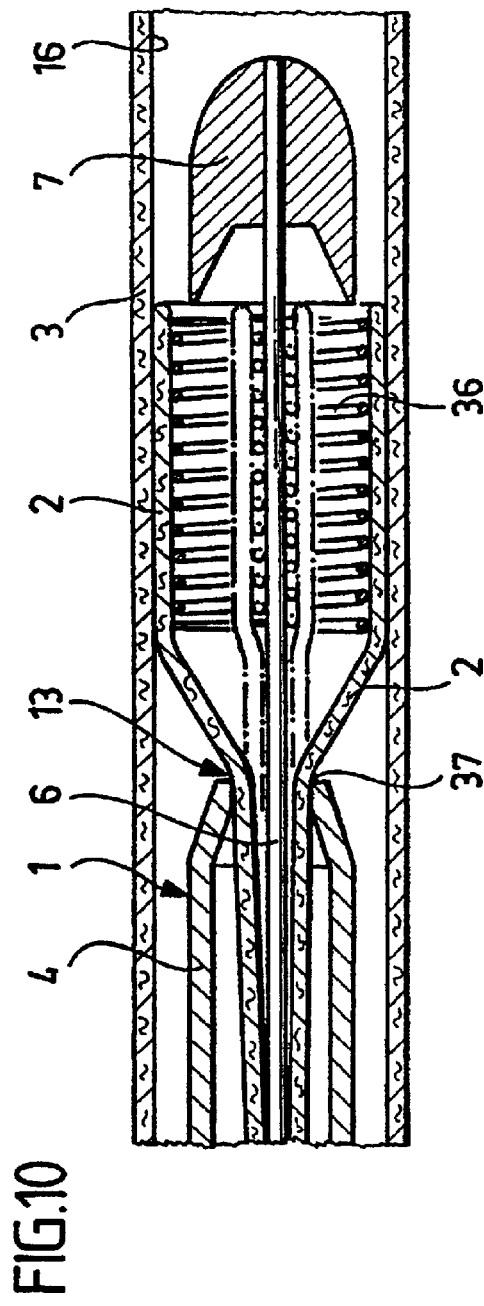
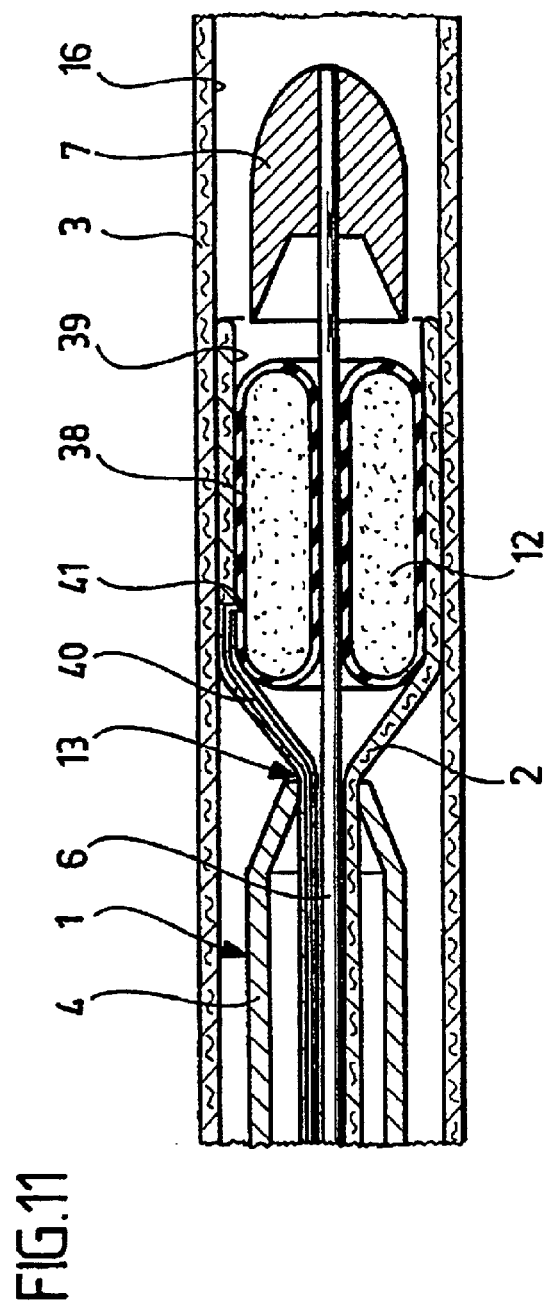
FIG.10
FIG.11

INSERTION CATHETER FOR VASCULAR PROSTHESIS

This application is a continuation of international application number PCT/EP00/07354 filed on Jul. 29, 2000.

The present disclosure relates to the subject matter disclosed in international application No. PCT/EP00/07354 of Jul. 29, 2000, which is incorporated herein by reference in its entirety and for all purposes.

BACKGROUND OF THE INVENTION

The invention relates to an insertion catheter for inserting a vascular prosthesis into a vessel, with an elongate, substantially tubular catheter cover having a proximal and a distal end, with an outlet for the vascular prosthesis provided at the distal end.

Vascular supports, i.e., so-called stents or stent grafts comprising metallic supporting structures which may also be covered with fabric are presently in use for treating vascular occlusions in humans, in particular, in the peripheral area of the human body, or also for eliminating abdominal and thoracic aortic aneurysms. These supporting structures are placed endoluminally by means of a catheter in the affected vascular segment.

The stents or stent grafts are mounted in a compressed, unexpanded state on the catheter and may be surrounded by a protective tubular cover which prior to insertion of the implant is retracted in order to release the latter. The vascular support assumes its final shape either by way of self-expansion owing to its plastic supporting structure or by being mounted on a balloon which transfers the vascular support into its opened shape by way of forced expansion.

Such supporting structures have the drawback that owing to an interaction between the metallic support and the fabric cover under dynamic stress the cover may suffer damage and cause endoleakages to occur.

To prevent such wear, vascular prostheses may also be used without any metallic or other supporting structure. These have the additional advantage that in vessels with low flow rates additional obstructions in the form of supporting structures do not act to cause occlusions. In particular, thin-walled prostheses are used with advantage and these are fitted with a balloon to the prepared vessel wall. In the case of such vascular prostheses having no supporting structure there is, however, the danger that when inserting these a section thereof will become twisted and result in closure of the vascular prosthesis. A safe and defined insertion of such vascular prostheses cannot be fully guaranteed with insertion catheters of the kind described at the outset.

The object of the present invention is, therefore, to so design an insertion catheter of the kind described at the outset that a vascular prosthesis can be inserted in a particularly simple and safe way into a vessel of the human body without causing closure of the vascular prosthesis by, for example, twisting.

SUMMARY OF THE INVENTION

This object is accomplished in accordance with the invention in that the outlet has a cross-sectional shape differing from a circular shape, and that the cross-sectional area defined by the outlet is smaller than the cross-sectional area of the vascular prosthesis inserted in the vessel in the opened, unexpanded state.

In conventional catheters the outlet is of circular cross section. A defined guidance of the vascular prosthesis during insertion is therefore not possible when the vascular prosthesis is released by retracting the catheter cover from the catheter. Owing to the shape of the outlet differing from the circular shape, completely irrespective of the cross-sectional shape as such, preferred directions are set which define a targeted guidance of the vascular prosthesis upon retracting the catheter cover. The outlet thus corresponds to the circumference of a circle defined by the circular shape, but, in principle, can have any cross section differing from the circular shape. The position of the catheter, in particular, a rotation thereof, can thereby be determined at any time, and an unintentional twisting of the vascular prosthesis can be counteracted at any time. This counteractive rotation can even prove completely unnecessary if an appropriate choice is made for the shape of the outlet, for the special shape does, in principle, already prevent a rotation of the vascular prosthesis by way of the guidance thereby provided.

It may be of particular advantage for the outer contour of the outlet to have a circumferential length corresponding at least to the circumference of the vascular prosthesis inserted in the vessel. This embodiment makes it possible for the vascular prosthesis to rest with its outer surface completely on the inside wall of the outlet without the vascular prosthesis having to be folded. The vascular prosthesis is therefore guided in a defined manner as it slides out of the catheter cover through the outlet over its entire circumference, and a twisting of the prosthesis is thus prevented.

Provision may be made in another preferred embodiment for the outer contour of the outlet to have a circumferential length which is smaller than the outer circumference of the vascular prosthesis inserted in the vessel. Such an outlet only allows the prosthesis to slide out of the catheter when the vascular prosthesis is folded. Owing to the non-circular shape, the folded prosthesis is nevertheless always guided so as to be secured against twisting, and a folded prosthesis can be arranged in a particularly compact way within the catheter. This is of advantage, in particular, in the case of vessels with a very small diameter.

It is expedient for the outlet to have the shape of a rectangle which has a shorter side edge with a width corresponding at least to an even-numbered multiple of a wall thickness of the vascular prosthesis. Two pairs of opposite edges of the outlet of different lengths are predetermined by the rectangular shape and enable a defined guidance of a folded prosthesis in a particularly simple way. The choice of the width of the rectangle in relation to the thickness of the wall of the prosthesis allows only prostheses which are folded in a specific way to pass out through the outlet. This provides an additional securing against twisting in that merely prostheses which are folded so as to prevent twisting can be introduced into the vessel.

Provision may advantageously be made for the cross-sectional area of the outlet area to be substantially identical to the cross-sectional area of a vascular prosthesis which is folded to its smallest possible cross section and is to be brought out through the outlet area. Such an outlet enables a defined guidance of the folded prosthesis on all sides because the outlet is in contact throughout its entire circumference with outwardly pointing parts of the prosthesis.

It is particularly advantageous for the distal end to comprise a guide body. The guide body facilitates introduction of the catheter into the vessel and owing to its arrangement at the distal end protects the outlet during the insertion into the vessel.

It is conceivable for the guide body to be movable, for example, pivotable, in any direction relative to the catheter cover. Provision is, however, advantageously made for the guide body to be displaceable relative to the catheter cover in a longitudinal direction predetermined by the catheter cover. This makes it possible to optionally vary the spacing between the guide body and the outlet, which is, for example, purposeful when the guide body serves to hold the prosthesis on the vessel wall.

In principle, there are various possibilities for arranging the guide body, for example, on the catheter cover, however, it is particularly advantageous for the guide body to be arranged at the end of a guide rod extending through the catheter cover. The guide body can be moved by the guide rod independently of the catheter cover.

It is expedient to provide a holding body for holding the prosthesis. This may be arranged on the catheter cover or the guide body. However, it is particularly advantageous for at least one holding body which is alterable in its outer circumference in a radial direction to be arranged in the area of the guide body on the guide rod. With this, the prosthesis can be prefixed on the inside wall of the vessel until it is finally joined to it, for example, by an anastomosis.

Provision is advantageously made for at least one holding body which is alterable in its outer circumference in a radial direction to be arranged in the area of the guide body on the vascular prosthesis. Such a holding body, in particular, when it is arranged on an inside circumferential wall of the vascular prosthesis, can, when it changes, preferably increases, its outer circumference, press the vascular prosthesis against an inside circumferential wall of the vessel and in this way at least temporarily fix the vascular prosthesis on the vessel.

Provision may be made in an advantageous embodiment for the holding body to be formed by a self-expanding vascular support. Such a vascular support, also referred to, for example, as stent, can increase its outer circumference, for example, by a fabric forming the stent unfolding or a compressed helical spring expanding.

It is expedient for the vascular support to be formed by a metal. Such a vascular support is particularly stable, and, in addition, if special alloys are used, can have a memory effect so that the vascular support can also change its outer circumference as a result of a change in temperature.

It is particularly expedient for the holding body to be inflatable by a fluid. With such a construction, one can dispense with complicated mechanical constructions, for example, radially protruding pins which are alterable in their length.

Provision may preferably be made for the holding body to comprise a balloon. In the deflated state, a balloon takes up particularly little space. In the inflated state, it can assume virtually any shape. In addition, a balloon is particularly atraumatic.

Provision is advantageously made for a fluid line which is in fluid communication with the interior of the holding body to extend within the guide rod. In this way, a separate feed line outside the catheter cover is unnecessary. The guide rod thus carries out a double function, which reduces the number of parts of the catheter.

In principle, it is conceivable to arrange the holding body on one side on the guide rod. It is, however, particularly advantageous for the holding body to surround the guide rod in the shape of a ring, as the prosthesis can then be pressed uniformly and symmetrically against the inside wall of the vessel.

All conceivable shapes are, in principle, possible for the ends of the catheter cover and the guide body which face each other. However, provision is made in accordance with a preferred embodiment for the distal end of the catheter cover and a proximal end of the guide body to have a complementary shape. The guide body and the catheter cover can thereby form a compact shape, which offers advantages, in particular, when introducing the catheter into the vessel as parts protruding from the catheter can unintentionally damage the vessel.

It is particularly expedient for the distal end of the catheter cover to be formed by an outer cone and the proximal end of the guide body by an inner cone. If the guide body is moved away from the outlet of the catheter, the distal end of the catheter cover then still forms a substantially blunt end which will normally not damage the vessel.

Although the guide body could also have a cornered distal end, it is particularly advantageous for the distal end of the guide body to have a rounded-off tip. This reduces the risk of damaging the vessel when introducing the catheter.

In principle, the guide body and the catheter cover could be spaced in any position relative to each other, but provision is advantageously made for the distal end of the catheter cover to be closable by the guide body. It is thus possible to make available a catheter which is completely closed at its distal end, and which, in addition, can have a completely smooth outer skin.

Provision may be made in accordance with a preferred embodiment of the invention for at least two substantially rod-shaped clamping fingers whose distal ends point in the direction towards the guide body to be arranged at the distal end of the catheter cover. The clamping fingers assist the function of the specially shaped outlet by prolonging the outlet at least partly in the direction of the guide body and thereby additionally guiding the vascular prosthesis.

In principle, it is conceivable for the clamping fingers to protrude unprotected from the catheter cover, however, it is expedient for clamping finger receptacles for receiving the distal ends of the clamping fingers to be provided on the guide body. When introducing the catheter into the vessel, the ends of the clamping fingers are hidden in the guide body, which minimizes the danger of damage to the vessel.

In principle, clamping fingers which are movable in the longitudinal direction of the catheter cover are also conceivable. However, it is particularly advantageous for the distal end of the clamping fingers to be movable in a radial direction. Clamping fingers movable in this way make it possible to widen the outlet partially delimited by the clamping fingers practically infinitely or at least in sections up to the maximum inside diameter of the vascular prosthesis, with guidance of the prosthesis being assured at all times.

Provision may preferably be made for the clamping fingers to be pivotable away from an axis of symmetry of the vessel in the direction towards an inside wall of the vessel. In this way, the clamping fingers arranged on the catheter cover form a kind of funnel and guide the prosthesis during the transition from the shape in which it passes through the outlet to the opened state.

The catheter may be hollow and smooth inside. It is, however, particularly advantageous for an inside guide for the vascular prosthesis to extend within the catheter cover, for the inside guide to be arranged inside the vascular prosthesis located within the insertion catheter and for the inside guide to have a cross-sectional shape which is geometrically similar to the outlet at least in the area of the outlet. The prosthesis thus surrounds the inside guide and is shaped owing to the shaping of the inside guide in such a way that the exiting from the catheter cover is particularly easy. Furthermore, the inside guide already prevents twisting of the prosthesis within the catheter cover. Even if it were twisted, the prosthesis would be returned to the desired shape again by the inside guide.

It may be expedient for the inside guide to extend essentially over the entire length of the catheter cover. In this way, the prosthesis is guided so as to be secured against twisting during the entire inserting procedure.

In principle, it is possible for the outlet to have only convex curvature areas. It is, however, particularly advantageous for the outer contour of the outlet to have concave and convex curvature areas. This results in formation of a structured contour of the outlet, which has significantly improved guiding characteristics as compared with a purely convex curvature, as the concave curvature areas project further into the outlet than the convex ones.

It is particularly expedient for the clamping finger to be arranged adjacent to a concave curvature area of the outer contour of the outlet. The concave curvature areas inevitably project further into the outlet than the convex curvature areas. Owing to the arrangement of the clamping fingers, these inwardly projecting areas are extended beyond the outlet in the direction towards the guide body, and the shape of the prosthesis can be optimally guided up to its maximum opened state.

In order to avoid any formation of edges in the transition from the outlet to the clamping fingers, provision may be made for the clamping finger to form with part of its surface the concave curvature area. A seamless transition between outlet and clamping finger is thereby enabled.

The surface of the catheter cover can be completely smooth and unstructured. It is, however, particularly advantageous for the catheter cover to have an inside hollow cross-sectional area which is geometrically similar to the outlet at least in a section of the catheter cover. Such a shaping of the inside of the catheter cover optimizes passage of the prosthesis out of the outlet by the prosthesis already being brought into the necessary shape before exiting. Twisting is virtually impossible and unintentional obstruction of the prosthesis is therefore effectively prevented during the insertion.

In accordance with a further preferred embodiment of the invention, provision may be made for a device for folding the vascular prosthesis to extend inside the catheter cover in a section thereof adjacent to the outlet, whereby the vascular prosthesis is made to assume during passage through the outlet a cross-sectional shape necessary therefor. Such a device makes it possible to arrange the prosthesis in almost any way within the catheter cover and before it passes out through the outlet to bring it into the necessary shape therefor, namely to fold it such that the cross-sectional area then assumed by the prosthesis is smaller than that of the outlet. This saves time, in particular, when preparing the catheter, i.e., when introducing the prosthesis into the catheter, and requires less care during the preparation.

Provision may be made for the device for folding to be formed by guide projections protruding from an inside wall of the catheter cover. Such projections, for example, with their radial extent increasing continuously inwardly in the direction towards the outlet, permit folding during the retraction of the catheter cover. The folding and the insertion with a maximum security against unintentional twisting can thus be achieved in one operation.

The outside diameter of the catheter cover can be larger than the inside diameter of the vascular prosthesis, but it is particularly advantageous for the outside diameter of the catheter cover to be smaller than the inside diameter of the opened vascular prosthesis. The catheter cover can thereby be displaced free of friction inside an inserted vascular prosthesis.

In a further preferred embodiment of the invention, provision may be made for the outside diameter of the catheter cover to correspond to the outside diameter of the guide body. A completely smooth outer skin of the catheter is thereby achievable, as edged transitions and projections on the outer cover of the catheter would increase the risk of damage during introduction of the catheter into the vessel.

In principle, the catheter could have a rigid cover, but it is expedient for the catheter cover to be formed by an elastic tube. An elastic tube can be introduced within a vascular system also through curved vascular paths without damaging these.

Provision may also advantageously be made for the holding body to be partially radially delimited by the clamping fingers in an inserting position of the insertion catheter. The holding body located within the prosthesis can upon expansion in a radial direction press the prosthesis against the clamping fingers and thus additionally contribute towards guiding the prosthesis. In addition, the clamping fingers can be spread out radially outwardly by the holding body.

Furthermore, provision may advantageously be made for the holding body to be radially at least partially surrounded by the guide body in an inserting position of the insertion catheter. The holding body is thereby protected by the guide body during insertion of the catheter.

To insert the vascular prosthesis, the proximal end of the catheter can be gripped by an operator. For this purpose, provision is advantageously made for a grip part surrounding the catheter cover to be provided at the proximal end thereof. In this way, the operator can hold and guide the catheter safely.

For optimum guidance of the catheter by the operator it is advantageous for him to always be able to grip the catheter in the proximity of a point at which the catheter is introduced into the patient's body, in particular, for the catheter cover to be bendable. For this purpose, it is advantageous for the grip part to be displaceable relative to the catheter cover.

In a preferred embodiment of the invention provision may be made for radially inwardly protruding projections to be arranged on the grip part. Such projections increase the friction between grip part and catheter cover, and the operator can therefore guide the catheter safely and precisely at all times.

When retracting the catheter during insertion of the prosthesis a very long section of the catheter cover may protrude from the point of insertion on the patient's body. It may therefore be advantageous for the projections to be formed by knife blades sharpened in the direction towards the distal end.

These enable splitting of the catheter cover so that the interior of the catheter cover is particularly easily accessible and the catheter cover is particularly easily removable again from the vessel. Furthermore, the maximum length of the guide rod, which should actually be twice as long as the catheter cover, is thereby reduced to a length corresponding approximately to the length of the catheter cover.

It may be particularly advantageous for the outlet to essentially have a dog's bone shape.

In another embodiment provision may be made for the outlet to essentially have a mushroom shape.

It may also be expedient for the outlet to essentially have a cloverleaf shape.

For optimized guidance, it can be advantageous for the cloverleaf shape to have leaves of different sizes.

On the other hand, it may also be expedient for the outlet to essentially have the shape of a cross with rounded-off edges.

In a further preferred embodiment, however, provision may also be made for the outlet to essentially have a crescent or half-moon shape.

The following description of preferred embodiments of the invention serves in conjunction with the drawings to explain the invention in greater detail.

BRIEF DESCRIPTION OF THE DRAWINGS

FIG. 1 shows a longitudinal section through the distal end of an insertion catheter during insertion into a vessel;

FIG. 2 shows a longitudinal section through a vessel and the end of the catheter with an inflated holding body;

FIG. 3 shows a cross section of a first embodiment of an outlet taken along line 3—3 from FIG. 2;

FIG. 4 is a sectional view corresponding to FIG. 3 through a second embodiment of an outlet;

FIG. 5 is a sectional view similar to FIG. 1 through a catheter with an alternative arrangement of the holding body;

FIG. 6 shows a longitudinal section similar to FIG. 1, but with clamping fingers arranged on the catheter cover;

FIG. 7 shows a cross section taken along line 7—7 from FIG. 6;

FIG. 7a shows a cross section taken along line 7—7 with an inflated holding body;

FIG. 7b shows a cross section taken along line 7b—7b from FIG. 6;

FIG. 10 shows a longitudinal section similar to FIG. 2, but with a self-expanding stent as holding body; and FIG. 11 shows a longitudinal section similar to FIG. 10, but with an inflatable holding body arranged on the vascular prosthesis.

DETAILED DESCRIPTION OF THE INVENTION

Figure 8:
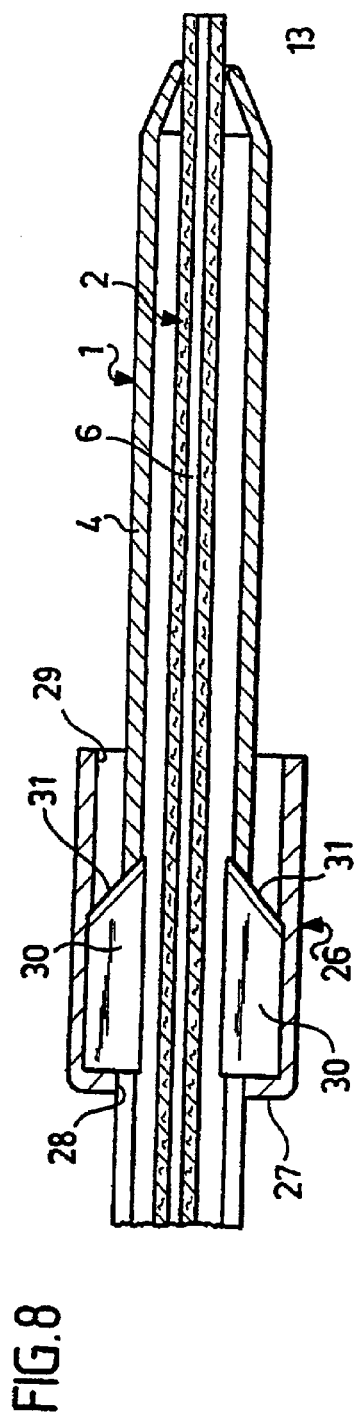
FIG. 8 shows a longitudinal section through the proximal end of a catheter.

Several variants of an insertion catheter generally designated 1 for introducing a vascular prosthesis 2 into a vessel 3 are shown in FIGS. 1 to 11. For reasons of clarity, identical parts have the same reference numerals.

The insertion catheter 1 essentially consists of a tubular catheter cover 4 having a constant cross section over almost its entire length. The catheter cover 4 tapers conically at its distal end so that this end has the shape of an outer cone 5. The wall thickness of the catheter cover 4 is substantially constant over the entire length of the catheter cover 4.

A guide rod 6 extends through the catheter cover 4 along its axis of symmetry. A guide body 7 is arranged at the distal end of the guide rod 6. The distal end of the guide body 7 is rounded off in the shape of a hemisphere. The proximal end is in the form of an inner cone 8 which is complementary to the outer cone 5 so that the distal end of the catheter cover 4 is insertable with a positive fit into the proximal end of the guide body 7. The diameter of the guide body 7 corresponds in its cross section to that of the catheter cover 4 so that a completely smooth outer skin of the catheter 1 is formed when the catheter cover 4 is inserted in the guide body 7.

The guide rod 6 is surrounded on a section thereof bordering on the guide body 7 and having approximately its length by a balloon 9 in the shape of a ring. The balloon 9 is in fluid communication with a channel 11 extending in the guide rod 6 via a transverse bore 10. The channel 11 can be fed from the proximal end of the guide rod 6 with a fluid 12 so that the balloon 9 passes from a deflated state in which it rests substantially completely against the guide rod 6, as shown in FIG. 1, into an inflated state in which it takes on a substantially cylindrical shape and its outer diameter then corresponds substantially to an inside diameter of the vessel 3, as shown in FIG. 2.

Finally, the vascular prosthesis 2 is arranged inside the catheter cover 4 such that it surrounds both the guide rod 6 and the balloon 9 completely.

At the distal end of the catheter cover 4, the catheter 1 has an outlet 13 formed essentially by an elongate slot 14 which, in turn, has a width corresponding substantially to twice the thickness of the wall of the vascular prosthesis 2. Outward curves 15 are located opposite each other in the central area of the outlet 13 so that the once folded vascular prosthesis 2 surrounding the guide rod 6 can be drawn through the slot 14.

To insert the vascular prosthesis 2, the catheter 1 is introduced into the vessel 3 until the vascular prosthesis 2 fully covers, for example, a fragile place on the vessel 3. The catheter cover 4 is drawn back relative to the vascular prosthesis 2 and the guide rod 6 until the balloon 9, which is originally located inside the catheter cover 4, has exited completely from the catheter cover 4.

The fluid 12, for example, an isotonic saline solution, is then passed through the channel 11 into the balloon 9 until it is inflated to such an extent that with its outer circumferential surface it presses the vascular prosthesis 2 against an inside wall 16 of the vessel 3 and holds it there. The catheter cover 4 is then drawn back step-by-step until the vascular prosthesis 2 is completely released and rests against the inside wall 16. Finally, the balloon 9 is deflated by letting off the fluid 12 and the guide rod 6 is retracted together with the guide body 7. The vascular prosthesis 2 can be optionally fixed to the vessel 3 by an anastomosis, not shown, by, for example, clips or suturing.

FIG. 4 shows a second example of a possible outlet 13 which has the shape of a rectangle 17. A shorter side and hence the width of the rectangle 17 corresponds to approximately four times the thickness of the wall of the vascular prosthesis 2. The cross-sectional area of the rectangle 17 is of such dimensions that the twice folded vascular prosthesis 2 surrounds the guide rod 6 and in its entirety takes up a minimum cross section. Only in this folded state can the vascular prosthesis 2 pass through the outlet 13 in the form of the rectangle 17. Prior to introduction of the insertion catheter 1, the vascular prosthesis 2 can already be brought in this folded state into the interior of the catheter cover 4, or just prior to exiting, it can be folded by guide projections, not shown, inside the catheter cover 4, which face the outlet 13.

An alternative embodiment of a guide body 18 is shown in FIG. 5. It differs from the guide body 7 in FIG. 1 in that a blind hole bore 19 almost completely penetrating the guide body 18 extends from its proximal end, and, in turn, is penetrated by the guide rod 6 which is connected to the tip of the guide body 18. In the inserting position of the catheter 1, the balloon 9 surrounding the guide rod 6 is located completely inside the blind hole bore 19 and is therefore surrounded and protected over its entire length by the guide body 18.

Insertion of a vascular prosthesis 2 into a vessel 3 with an insertion catheter 1, as shown in FIG. 5, is carried out in accordance with the principle already described hereinabove. It must, however, be taken into consideration that the guide body 18 is designed so as to be movable relative to the guide rod 6 so that prior to inflation of the balloon 9, the guide body 18 is moved away from the balloon 9 in a distal direction in order that the latter can press the vascular prosthesis 2 against the inside wall of the vessel 3 before the vascular prosthesis 2 is positioned inside the vessel 3 by drawing back the catheter cover 4.

FIGS. 6 and 7 show a modified embodiment of the insertion catheter 1. At the distal end of the catheter cover 4 four guiding rods 20 are arranged in concave curvature areas of the essentially cloverleaf-shaped outlet 13 so as to project in the longitudinal direction of the catheter cover 4. In the inserting position of the insertion catheter 1, guiding rod ends 21 are inserted in corresponding blind-hole-like guiding rod receptacles 22 of a bullet-shaped guide body 23.

Inside the catheter cover 4, an inside guide 24 of cross-shaped cross section is arranged so as to extend along the axis of symmetry of the catheter cover 4 and beyond the distal end of the catheter cover 4 as far as the proximal end of the guide body 23. In the area of the guiding rods 20, this inside guide 24 is surrounded by a balloon 9, which in its deflated state, as shown in FIG. 7, also assumes the shape of a cross. The inside guide 24 and hence also the balloon 9 in the area of the guiding rods 20 are surrounded by the vascular prosthesis 2 which rests against the inside guide 24 and also assumes the shape of a cross. In the interior, the catheter cover 4 is of complementary shape, but is at a distance from the inside guide 24 so that a gap remains between the inside guide 24 and an inside catheter wall 25 and is filled out by the vascular prosthesis 2.

To insert the vascular prosthesis 2, the insertion catheter 1 is introduced in its inserting position into the vessel 3 with the guiding rods 20 inserted in the guide body 23. Once the final position for the vascular prosthesis 2 is reached, the catheter cover 4 is drawn back in a proximal direction until the guiding rod ends 21 have emerged from the guiding rod receptacles 22. The balloon 9 is then inflated by introducing a fluid 12, whereby it assumes a substantially circular cross-sectional shape and thereby pivots the guiding rods 20 away from the axis of symmetry of the catheter cover 4 in the direction towards the inside wall 16 of the vessel 3. In this way, the transition of the vascular prosthesis 2 exiting from the outlet 13 in the shape of a cloverleaf is guided continuously by the guiding rods 20 until the vascular prosthesis 2 assumes a substantially circular cross section and rests against the inside wall 16 of the vessel 3. FIG. 7a shows the expanded position of the guiding rods 20 in cross section. The guiding rods 20 thus constitute a partial extension of the outlet 13 for guiding the vascular prosthesis 2 during the insertion.

At its proximal end, the insertion catheter 1 has a sleeve-shaped grip 26 whose inside diameter is somewhat larger than the outside diameter of the catheter cover 4. A proximal grip end 27 of the grip 26 is closed but has a central bore 28 whose inside diameter corresponds to the outside diameter of the catheter cover 4 so that the grip 26 can slide free of play on the catheter cover 4. Projecting radially inwardly from an inside grip wall 29 are two knives 30 which each have a blade 31 inclined in the direction towards the distal end of the catheter cover 4. The knives 30 project radially just to such an extent that they completely penetrate the catheter cover 4, but do not touch and therefore also not damage the vascular prosthesis 2 arranged inside the catheter cover 4.

The special design of the grip 26 serves to split the catheter cover 4 during the retraction and to thereby facilitate removal of the same from the vessel 3. In particular, the guide rod 6 or the inside guide 24 is thereby always accessible and operable by the operator also when the catheter cover 4 is retracted.

Figure 9A:
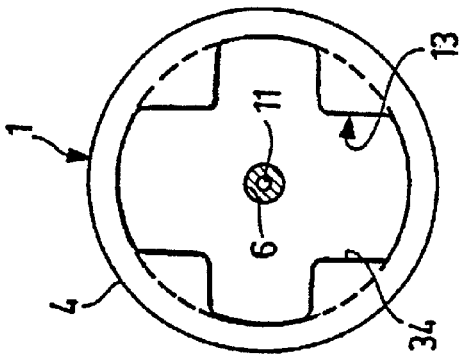
FIGS. 9a to 9c show alternative embodiments of the outlet.
Figure 9B:
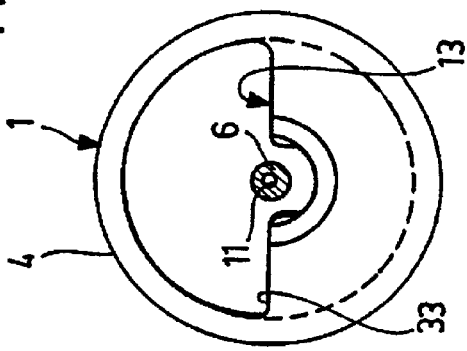
Figure 9C:
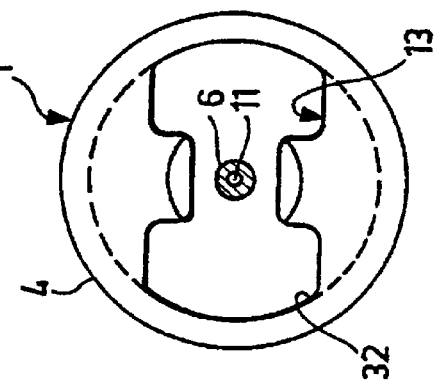

FIGS. 9a, 9b and 9c show schematically further shapes of outlets 13 of the insertion catheter 1. FIG. 9a shows a dog's bone shape 32, FIG. 9b a mushroom shape 33 and FIG. 9c a cloverleaf shape 34, in which opposite leaf-like bulges are of identical design, but pairs of which have a different size.

Guiding rods 20, each arranged in concave curvature areas of the outlets 32 to 34, may also be provided in conjunction with the outlets 32 to 34. Furthermore, inside guides 24 of geometrically similar shape are possible in conjunction with the outlets 32 to 34. A complementary shaping of the inside catheter wall 25 is, of course, possible. It is owing to this complementary shaping of catheter wall 25 and inside guide 24, which, as it were, form a folding device, that the folding of the vascular prosthesis 2 is possible when the latter passes through one of the outlets 32 to 34 by retraction of the catheter cover 4. In this way, radially inwardly protruding areas of the catheter wall 25 form guide projections 35 for folding the vascular prosthesis 2.

FIG. 10 shows a longitudinal section similar to FIG. 2, but instead of the balloon 9 a self-expanding stent 36 is provided. The stent 36 can, for example, be formed from metal or a special memory metal which upon insertion of the insertion catheter 1 into the vessel 3 rests substantially against the guide rod 6, undergoes deformation owing to thermal activation and thereby assumes a larger diameter to hold the vascular prosthesis 2 and simultaneously press the same against the inside wall 16 of the vessel 3. The stent 36 can be selectively completely integrated into the vascular prosthesis 2 or arranged on an outer circumferential wall thereof.

However, FIG. 10 shows the arrangement of the stent 36 only purely schematically, so that in one embodiment it can be arranged on the guide rod 6, but in another embodiment on the vascular prosthesis 2.

A further difference from the insertion catheter 1 shown in FIG. 2 is that the outlet 13 has a half-moon-shaped cross-sectional area 37. However, any other shapes of the cross-sectional area 37 are also conceivable, for example, also those described in conjunction with FIGS. 9a, 9b and 9c.

FIG. 11 shows a longitudinal section similar to FIG. 2. A ring-shaped balloon 38 arranged on an inside prosthesis wall 39 of the vascular prosthesis 2 is provided as holding body. The balloon 38 is inflatable by allowing a fluid 12 to flow in via a channel 40 which extends from proximal to distal in the wall of the vascular prosthesis 2 and is in fluid communication with the balloon 38 via a radially inwardly oriented transverse connection 41. The balloon 38, which is not fixedly connected to the guide rod 6, is supported during the inflating and in its inflated state solely on the guide rod 6 so that the vascular prosthesis 2 is held on the inside wall 16 of the vessel 3.

The arrangement of the holding body is shown merely schematically in FIG. 11. The surface of the balloon 38 facing away from the inside prosthesis wall 39 itself forms part of the inside prosthesis wall. Alternatively, it is conceivable to integrate the balloon 38 into the wall of the vascular prosthesis 2 so that during the inflating of the balloon 38, the thickness of the wall of the vascular prosthesis 2 changes, i.e., increases, and thereby holds the vascular prosthesis 2 on the vessel 3 without parts of the balloon 38 projecting into the inside of the vessel 3 after the deflating of the balloon 38 and preventing flow of a medium flowing in the vessel 3.

It is also conceivable to provide a stent 36 and a balloon 9 or 38 jointly, for example, in such a way that the stent 36 surrounds the balloon 38 or vice-versa, with the inflating of the balloon 9 or 38 simultaneously inflating the stent 36, but the latter can also be self-expanding.

The insertion of the vascular prosthesis 2 into the vessel 3 with the insertion catheters 1 described in conjunction with FIGS. 10 and 11 is carried out essentially in the same way as already described hereinabove, in particular, in conjunction with FIGS. 1 and 2.

What is claimed is:

1. Insertion catheter carrying a vascular prosthesis without a supporting structure for insertion of said vascular prosthesis into a vessel, with an elongate, substantially tubular catheter cover having a proximal end and a distal end, an outlet for said vascular prosthesis being provided at said distal end, said outlet having a cross-sectional shape differing from a circular shape, and the cross-sectional area defined by said outlet being smaller than the cross-sectional area of said vascular prosthesis inserted in said vessel in the opened, unexpanded state, wherein a device for folding said vascular prosthesis extends inside said catheter cover in a section thereof adjoining said outlet, so that said vascular prosthesis on passing through said outlet assumes a cross-sectional shape required therefor.

2. Insertion catheter in accordance with claim 1, wherein the outer contour of said outlet has a circumferential length corresponding at least to the circumference of said vascular prosthesis inserted in said vessel.

3. Insertion catheter in accordance with claim 1, wherein the outer contour of said outlet has a circumferential length which is smaller than the outer circumference of said vascular prosthesis inserted in said vessel.

4. Insertion catheter in accordance with claim 3, wherein said outlet has the shape of a rectangle which has a shorter side edge with a width corresponding at least to an even-numbered multiple of a wall thickness of said vascular prosthesis.

5. Insertion catheter in accordance with claim 3, wherein the cross-sectional area of said outlet is substantially identical to the cross-sectional area of a vascular prosthesis which is folded to its smallest possible cross section and is to be brought out through the outlet area.

6. Insertion catheter in accordance with claim 1, wherein the distal end comprises a guide body.

7. Insertion catheter in accordance with claim 6, wherein said guide body is displaceable relative to said catheter cover in a longitudinal direction predetermined by said catheter cover.

8. Insertion catheter in accordance with claim 6, wherein said guide body is arranged at the end of a guide rod extending through said catheter cover.

9. Insertion catheter in accordance with claim 8, wherein at least one holding body alterable in a radial direction in its outer circumference is arranged on said guide rod in the area of said guide body.

10. Insertion catheter in accordance with claim 8, wherein at least one holding body alterable in a radial direction in its outer circumference is arranged on said vascular prosthesis in the area of said guide body.

11. Insertion catheter in accordance with claim 10, wherein said holding body comprises a self-expanding vascular support.

12. Insertion catheter in accordance with claim 11, wherein said vascular support is formed by a metal.

13. Insertion catheter in accordance with claim 9, wherein said holding body is inflatable by means of a fluid.

14. Insertion catheter in accordance with claim 13, wherein said holding body comprises a balloon.

15. Insertion catheter in accordance with claim 13, wherein a fluid line which is in fluid communication with the interior of said holding body extends within said guide rod.

16. Insertion catheter in accordance with claim 9, wherein said holding body surrounds said guide rod in the shape of a ring.

17. Insertion catheter in accordance with claim 6, wherein said distal end of said catheter cover and a proximal end of said guide body have a complementary shape.

18. Insertion catheter in accordance with claim 17, wherein said distal end of said catheter cover is formed by an outer cone and said proximal end of said guide body by an inner cone.

19. Insertion catheter in accordance with claim 6, wherein said distal end of said guide body has a rounded-off tip.

20. Insertion catheter in accordance with claim 6, wherein said distal end of said catheter cover is closable by said guide body.

21. Insertion catheter in accordance with claim 6, wherein at least two substantially rod-shaped clamping fingers whose distal ends point in the direction towards said guide body are arranged at said distal end of said catheter cover.

22. Insertion catheter in accordance with claim 21, wherein clamping finger receptacles for receiving the distal ends of said clamping fingers are provided on said guide body.

23. Insertion catheter in accordance with claim 21, wherein the distal end of said clamping fingers is movable in a radial direction.

24. Insertion catheter in accordance with claim 23, wherein said clamping fingers are pivotable away from an axis of symmetry of said vessel in the direction towards an inside wall of said vessel.

25. Insertion catheter in accordance with claim 1, wherein an inside guide for said vascular prosthesis extends within said catheter cover, said inside guide is arranged in the interior of said vascular prosthesis located within said insertion catheter, and said inside guide has a cross-sectional shape which is geometrically similar to said outlet at least in the area of said outlet.

26. Insertion catheter in accordance with claim 6, wherein an inside guide for said vascular prosthesis extends within said catheter cover, said inside guide is arranged in the interior of said vascular prosthesis located within said insertion catheter, and said inside guide has a cross-sectional shape which is geometrically similar to said outlet at least in the area of said outlet.

27. Insertion catheter in accordance with claim 25, wherein said inside guide extends essentially over the entire length of said catheter cover.

28. Insertion catheter in accordance with claim 1, wherein the outer contour of said outlet has concave and convex curvature areas.

29. Insertion catheter in accordance with claim 28, wherein the clamping finger is arranged adjacent to a concave curvature area of the outer contour of said outlet.

30. Insertion catheter in accordance with claim 29, wherein said clamping finger forms with part of its surface said concave curvature area.

31. Insertion catheter in accordance with claim 1, wherein said catheter cover has an inside hollow cross-sectional area which is geometrically similar to said outlet at least in a section of said catheter cover.

32. Insertion catheter in accordance with claim 1, wherein said device for folding is formed by guide projections protruding from an inside wall of said catheter cover.

33. Insertion catheter in accordance with claim 1, wherein the outside diameter of said catheter cover is smaller than the inside diameter of said opened vascular prosthesis.

34. Insertion catheter in accordance with claim 6, wherein the outside diameter of said catheter cover corresponds to the outside diameter of said guide body.

35. Insertion catheter in accordance with claim 1, wherein said catheter cover is formed by an elastic tube.

36. Insertion catheter in accordance with claim 19, wherein said holding body is radially partially delimited by said clamping fingers in an inserting position of said insertion catheter.

37. Insertion catheter in accordance with claim 21, wherein said holding body is radially at least partially surrounded by said guide body in an inserting position of said insertion catheter.

38. Insertion catheter in accordance with claim 1, wherein a grip part surrounding said catheter cover is provided at the proximal end of said catheter cover.

39. Insertion catheter in accordance with claim 38, wherein said grip part is displaceable relative to said catheter cover.

40. Insertion catheter in accordance with claim 38, wherein radially inwardly protruding projections are arranged on said grip part.

41. Insertion catheter in accordance with claim 40, wherein said projections are formed by knife blades sharpened in the direction towards the distal end.

42. Insertion catheter in accordance with claim 33, wherein said outlet essentially has a dog's bone shape.

43. Insertion catheter in accordance with claim 33, wherein said outlet essentially has a mushroom shape.

44. Insertion catheter in accordance with claim 33, wherein said outlet essentially has a cloverleaf shape.

45. Insertion catheter in accordance with claim 44, wherein said cloverleaf shape has leaves of different sizes.

46. Insertion catheter in accordance with claim 33, wherein said outlet essentially has a cross shape with rounded-off edges.

47. Insertion catheter in accordance with claim 33, wherein said outlet essentially has a crescent or half-moon shape.

* * * * *